United States Patent [19]

Lerman

[11] 4,337,764
[45] Jul. 6, 1982

[54] ADJUSTABLE MOTION BRACE

[75] Inventor: Max Lerman, Beverly Hills, Calif.

[73] Assignee: United States Manufacturing Company, Pasadena, Calif.

[21] Appl. No.: 239,404

[22] Filed: Mar. 2, 1981

[51] Int. Cl.³ ............................................. A61F 5/00
[52] U.S. Cl. ................................... 128/80 F; 403/116
[58] Field of Search ............... 128/80 R, 80 F, 80 C, 128/88; 3/22, 24, 26, 27, 21; 403/116, 119, 95, 113

[56] References Cited

U.S. PATENT DOCUMENTS 3,528,412 9/1970 McDavid ........................ 128/80 C
3,779,654 12/1973 Horne .............................. 128/80 F
3,902,482 9/1975 Taylor ............................. 128/80 F Primary Examiner—John D. Yasko
Attorney, Agent, or Firm—Christie, Parker & Hale

[57] ABSTRACT

A brace for use as a knee joint brace or a fracture brace, for example, comprises upper and lower bars and at least one pivot pin for joining adjacent end portions of the bars so they can pivot relative to each other about at least one transverse axis. One embodiment comprises a polycentric brace in which adjacent end portions of the upper and lower bars are engaged with one another and pivot relative to each other about a pair of spaced-apart upper and lower pivot pins. A bracket protrudes outwardly beyond left and right edges of the upper bar, and a continuous arcuate groove extends through the bracket so that left and right portions of the groove extend beyond the left and right edges of the bar. Left and right stop pins are releasably inserted in the left and right portions of the groove, and the stop pins can be moved to independently desired locations in the groove and tightened by set screws to set the angle of travel of the upper bar.

2 Claims, 5 Drawing Figures

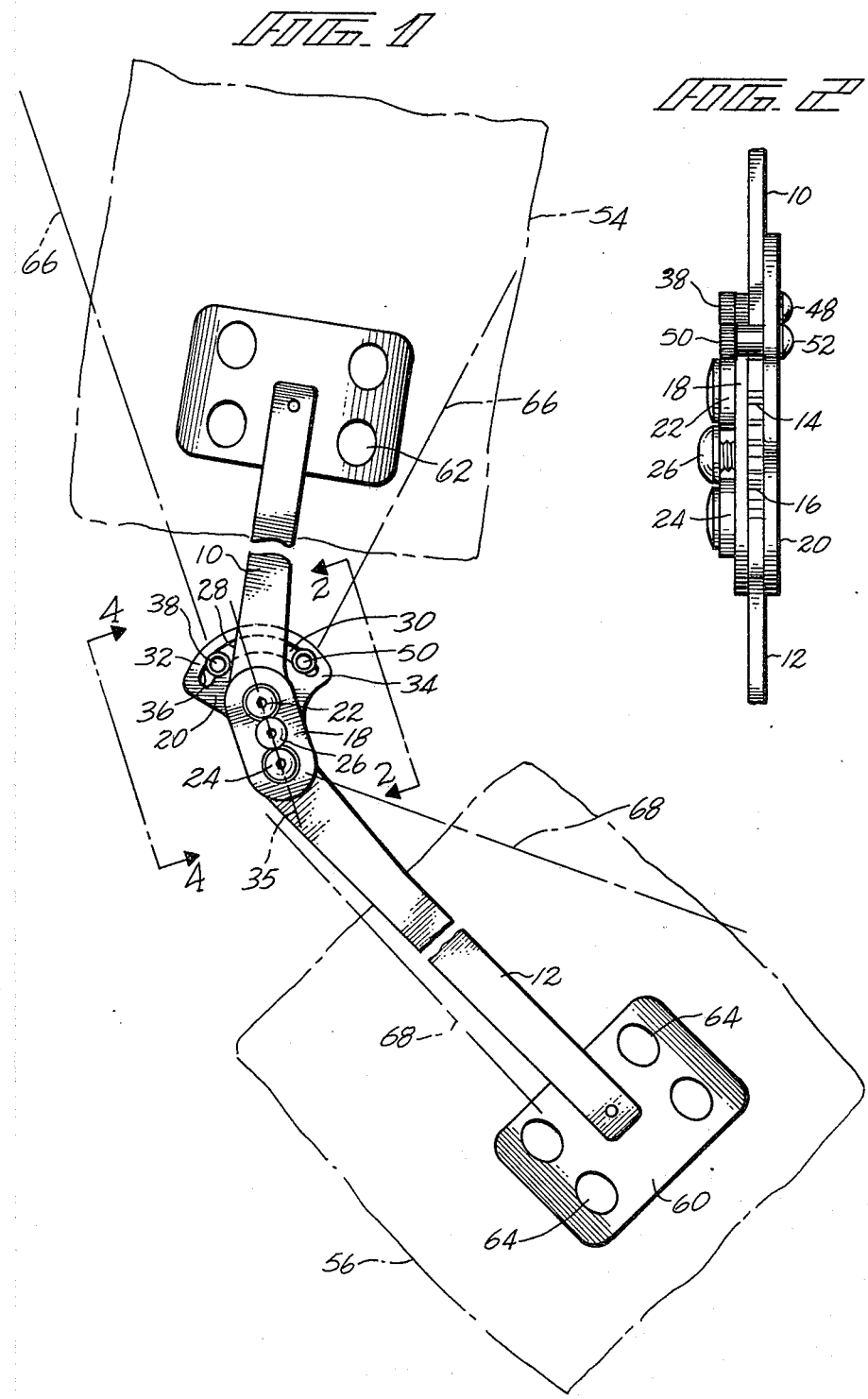

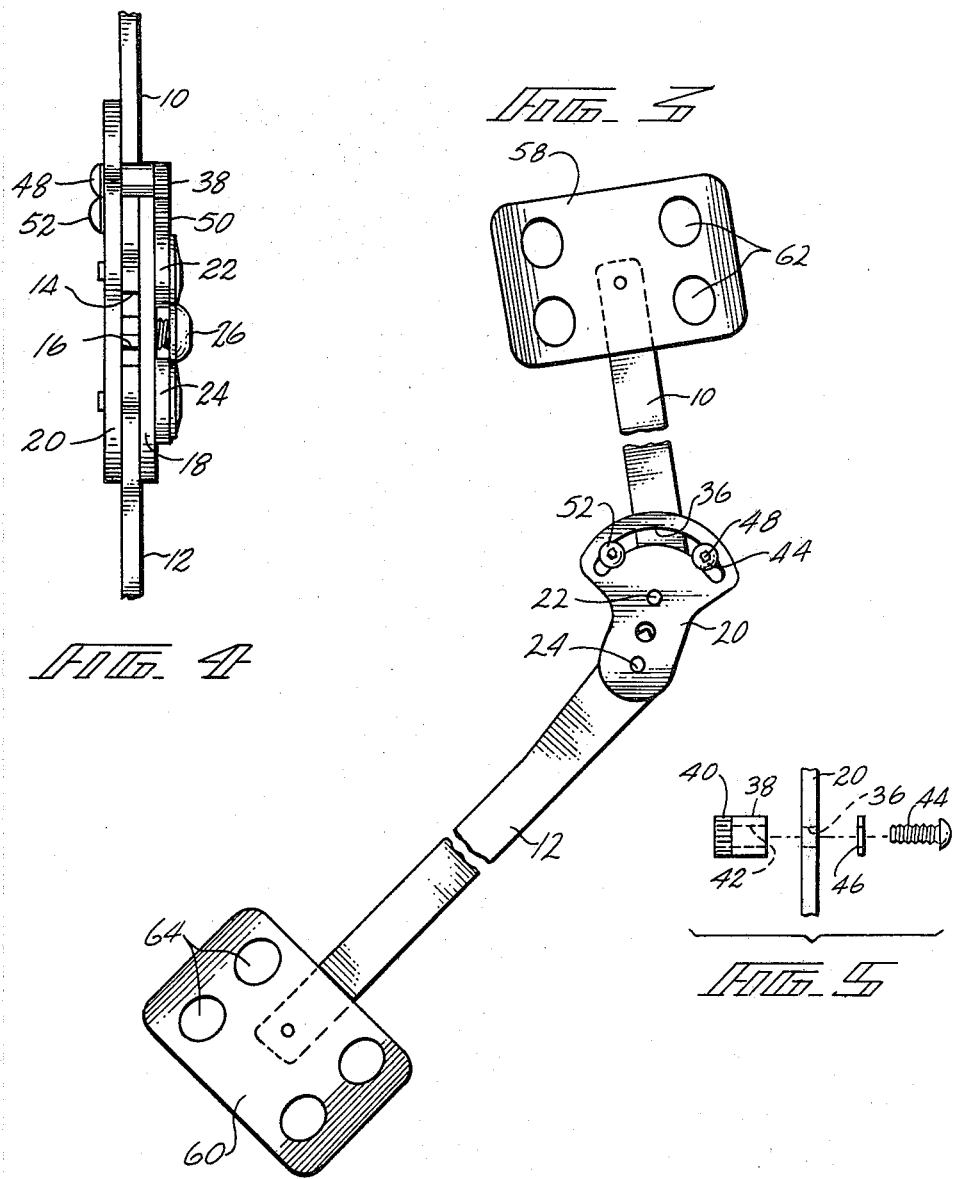

ADJUSTABLE MOTION BRACE

BACKGROUND OF THE INVENTION

1. Field of the Invention

This invention relates generally to braces, such as knee joint braces and fracture braces, for example; and more particularly to a brace that can be adjusted to control the range of bending motion of a joint during the healing process.

2. Description of the Prior Art

Knee joint braces are used to provide support for the knee joint during the process of healing from a ligament injury to the knee, for example. Such a brace has an upper bar attached to a cast placed around the patient's thigh and a lower bar attached to a cast placed around the patient's lower leg. The upper and lower bars are joined together to pivot about an axis through the knee joint. Such a knee joint brace provides the desired amount of firm support to prevent sidewise motion of the knee ligaments as they heal. The degree of angular travel of the upper and lower bars can be set to control the angle through which the patient can move his or her knee during the rehabilitation process. In some braces the angle of travel can be adjusted to provide for gradually greater bending motion of the knee joint during the rehabilitation process. That is, as the knee joint heals, it is desirable to gradually increase the range of angular motion, depending upon the degree of injury and the degree of healing.

The prior art has provided a number of braces that can be used to support a knee joint during healing. Some prior art knee braces, which have provided means of adjustment to increase bending motion of the knee during rehabilitation, have suffered from a number of disadvantages. Some of these braces are too complex and, therefore, too expensive to manufacture in a competitive market; or they are too large and cumbersome or not effectively adjustable to all desirable angles.

The present invention provides a brace that overcomes these disadvantages. The brace also has additional advantages described in detail below.

The adjustable brace of this invention is an improvement over the braces disclosed in the following patents:

| U. S. Pat. No. | Patentee |
|---|---|
| 2,410,560 | Witte |
| 2,570,382 | Ruetting |
| 3,528,412 | McDavid |
| 3,785,372 | Craig |
| 4,088,130 | Applegate |

In addition to its use as a knee joint brace with casts on the patient's upper and lower leg, the improvement provided by this invention also is adaptable for use with various fracture braces or other braces for supporting joints where controlled bending is desirable.

SUMMARY OF THE INVENTION

Briefly, one embodiment of this invention provides a brace having a first bar and a second bar and pivot means for adjoining adjacent portions of the first and second bars to allow the first and second bars to pivot relative to each other about an axis. A bracket overlies the adjacent portions of the first and second bars, and the bracket is rigidly secured to the first bar and second bar. The bracket extends toward the second bar to provide left and right protruding portions extending laterally away from respective left and right edges of the second bar. An elongated groove extends essentially continuously between the left and right protruding portions of the bracket. An adjustable left stop is releasably secured to a desired location in the portion of the groove on the left protruding portion of the bracket, so the left stop can engage the left edge of the second bar to limit motion in the left direction. A separate adjustable right stop is releasably secured to a desired location in the portion of the groove on the right protruding portion of the bracket, so the right stop can engage the right edge of the second bar to limit motion in the right direction. Thus, placement of the left and right stops can provide an infinite means of progressively adjusting the angular travel of the second bar relative to the first bar, so that bending motion of a patient's joint can be progressively increased during the healing process.

In one embodiment, the invention provides an effective means of controlling angular travel between first and second bars joined in a polycentric pivot arrangement, as described in more detail below.

These and other aspects of the invention will be more fully understood by referring to the following detailed description and the accompanying drawings.

DRAWINGS

FIG. 1 is a fragmentary front elevation view showing an adjustable motion brace according to principles of this invention;

FIG. 2 is a fragmentary side elevation view taken on line 2—2 of FIG. 1;

FIG. 3 is a fragmentary rear elevation view showing the opposite side of the brace shown in FIG. 1;

FIG. 4 is a fragmentary side elevation view taken on line 4—4 of FIG. 1; and

FIG. 5 is an exploded view showing a means for releasably securing a stop to the brace.

DETAILED DESCRIPTION

A brace according to principles of this invention includes a rigid, elongated, thin, flat upper bar 10 and a rigid, elongated, thin, flat lower bar 12. The upper and lower bars also can be referred to as first and second bars, or a thigh bar and a lower leg bar, in the case of use as a knee joint brace, for example.

Adjacent end portions of the two bars are connected so they can pivot relative to one another about at least one transverse axis. Although the invention can be used with a brace that pivots about a single axis, the invention is especially suitable in providing an effective means of controlling angular motion in a "polycentric" brace, in which the upper and lower bars pivot about a pair of spaced-apart upper and lower axes. In a polycentric brace, as one bar pivots it causes the other bar to pivot, and the axis about which the two bars pivot at any time changes. This better simulates the bending action of the knee joint than a brace that pivots about a single axis. Such polycentric braces are known, and examples of polycentric braces are those manufactured by Zinco Industries, Inc., Montrose, Calif.

Briefly, the polycentric pivot includes gear teeth 14 on the lower end of the upper bar that mesh with gear teeth 16 on the upper end of the lower bar. A narrow, rigid plate 18 overlies adjacent end portions of the upper and lower bars so as to cover the meshing gear teeth on one side of the brace. On the other side of the brace, a bracket 20 overlies adjacent end portions of the upper and lower bars so as to cover the meshing gear teeth on that side of the brace. The configuration of the bracket will be described in more detail below.

An upper pivot pin 22 extends through the plate 18, the lower end portion of the upper bar, and the upper portion of the bracket 20. The upper bar can pivot relative to the plate and the bracket about a transverse axis through the upper pivot pin 22. A lower pivot pin 24 extends through a lower portion of the plate 18, an upper portion of the lower bar, and a lower portion of the bracket. The lower bar can pivot relative to the plate and the bracket about a transverse axis through the lower pivot pin. Thus, the upper and lower bars pivot about corresponding spaced-apart transverse axes, and angular movement of one bar causes the other bar to also undergo angular movement through the connection between the two bars provided by the meshing gear teeth.

The heads of the pivot pins 22, 24 can be retained by a screw 26 threaded into a bore located between the pivot axes of the upper and lower pivot pins. The head of the screw overlaps outer relief portions of the upper and lower pivot pins to act as a retainer for the pivot pins.

The bracket 20 extends upwardly alongside opposite left and right edges 28, 30 of the upper bar 10. The bracket has left and right protruding portions 32, 34 that project outwardly away from the left and right edges of the upper bar, respectively. Stated another way, the left and right portions of the bracket protrude outwardly beyond the opposite sides of an axis 35 on which the pivot axes of the upper and lower pivot pins are aligned.

An elongated continuous arcuate groove 36 extends through the bracket. The axis of curvature of the groove is centered approximately at the midpoint between the pivot axes of the upper and lower pivot pins. The groove is sufficiently long that it can extend outwardly well beyond the left and right edges of the upper bar, as shown best in FIGS. 1 and 3.

A left stop pin 38 is releasably mounted in the left portion of the groove adjacent the left edge of the upper bar. As shown best in FIG. 5, the stop pin comprises a cylindrical receptacle with a knurled exterior upper surface 40 and a bore 42 extending entirely through it. An internally threaded portion of the bore closest to the groove in the bracket receives the externally threaded shank portion of a set screw 44 on the opposite side of the bracket. The set screw extends through a lock washer 46, which bears against the face of the bracket adjacent the groove. The set screw can have an Allen head opening 48 to permit loosening and tightening of the set screw relative to the threaded passage in the receptacle 38. Thus, the left stop pin can be moved to any desired position in the left portion of the groove adjacent the left edge of the upper stop bar and then tightened to hold it in a fixed position.

Similarly, a right stop pin 50 is mounted in the right portion of the groove adjacent the right edge of the upper bar. The right pivot pin is identical in construction to the left pivot pin, and its position in the right portion of the groove is adjusted by a right set screw 52, shown in FIG. 3.

In using the brace as a knee joint brace, an upper plaster cast 54 (shown in phantom lines in FIG. 1) is placed around the lower portion of a patient's thigh, and a lower plaster cast 56 (shown in phantom lines in FIG. 1) is placed around the patient's lower leg. An upper flange 58, rigidly affixed to the upper end of the upper bar, is placed over the upper plaster cast, and a similar lower flange 60 on the lower end of the lower bar is placed over the lower plaster cast 56. Bandages (not shown) are then wrapped around the upper and lower arms of the brace around the upper and lower plaster casts. The finished outer plaster casts (not shown) are then formed around the upper and lower flanges of the brace and around the wrapped portions of the upper and lower arms to form the finished cast. Holes 62 in the upper flange 58 and similar holes 64 in the lower flange 60 are filled with the Plaster of Paris material of the finished cast to act as rivets for securely fastening the upper and lower arms to the upper and lower casts.

The set screws of the left and right stop pins 38, 50 are then loosened and the stop pins are moved to desired locations in the groove adjacent the left and right edges of the upper bar. The left and right set screws are tightened to hold the stop pins in positions that control angular movement of the knee joint. That is, as the upper bar 10 moves to the right in FIG. 1, it engages the right stop pin 50 to prevent further angular travel in the right direction. Similarly, as the upper bar moves toward the left in FIG. 1, its left edge engages the left stop pin to limit further angular movement in the left direction. FIG. 1 shows the left and right stop pins at intermediate locations in the groove, which limits angular travel of the upper bar and the lower bar to angles defined by the phantom lines 66, 68, respectively, in FIG. 1. As the stop pins are moved farther outwardly from the edges of the upper and lower bars, these ranges of angular movement can be increased to provide progressively greater movement of the knee joint as rehabilitation progresses. One stop pin can be adjusted independently of the other stop pin, so that angular movement of the knee joint in the forward direction can be adjusted independently of angular motion of the knee in a rear direction.

Although the invention has been described in the context of a knee joint brace, it is to be understood that the invention also can be used with other types of braces, such as various fracture braces or supports for bodily joints, such as the knee or elbow joints. In addition, the brace described above could be modified so that the stop pins engage opposite edges of the lower bar of the brace, instead of the upper bar, without departing from the scope of the invention.

I claim:

1. A brace comprising a first bar; a second bar; pivot means for joining adjacent portions of the first and second bars to allow the first and second bars to pivot relative to each other about an axis; a bracket overlying said adjacent portions of the first and second bars; first means for rigidly securing the bracket to the first bar, the bracket extending away from the first bar toward the second bar; means for rigidly securing the bracket to the second bar; the bracket having left and right protruding portions extending laterally away from respective left and right edges of the second bar; an elongated continuous groove on the left protruding portion and the right protruding portion of the bracket; adjustable left stop means for being releasably secured to a desired location in the portion of the groove on the left protruding portion of the bracket so the second bar can engage the left stop means for limiting its travel in the left direction; and adjustable right stop means for being releasably secured to a desired location in the portion of the groove on the right protruding portion of the bracket so the second bar can engage the right stop means for limiting its travel in the right direction.

2. A brace comprising a first bar; a second bar; polycentric pivot means for joining adjacent end portions of the first and second bars to allow the first and second bars to pivot relative to each other about a pair of spaced-apart axes, said polycentric pivot means comprising means for engaging adjacent portions of the first and second bars, and first and second pivot means for allowing said adjacent portions of the first and second bars to pivot about spaced-apart first and second axes, respectively; a bracket overlying said adjacent portions of the first and second bars, the bracket extending away from said first bar toward the second bar to provide left and right protruding portions extending laterally away from respective left and right edges of the second bar; an elongated groove extending continuously along the left protruding portion and along the right protruding portion of the bracket; adjustable left stop means for being releasably secured to a desired location in the portion of the groove on the left protruding portion of the bracket so a left edge of the second bar can engage the left stop means to limit its angular travel in the left direction; and adjustable right stop means for being releasably secured to a desired location in a portion of the groove on the right protruding portion of the bracket so that a right edge of the upper bar can engage the right stop means to limit its angular travel in the right direction.

* * * * *